US006441151B1

(12) United States Patent
Gordon-Kamm et al.

(10) Patent No.: US 6,441,151 B1
(45) Date of Patent: Aug. 27, 2002

(54) PLANT PROHIBITION GENES AND THEIR USE

(75) Inventors: William J. Gordon-Kamm, Urbandale; Keith S. Lowe, Johnston, both of IA (US); Ramgopal Nadimpalli, Bloomfield, NJ (US); Carl R. Simmons, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/395,674

(22) Filed: Sep. 14, 1999

Related U.S. Application Data

(60) Provisional application No. 60/100,691, filed on Sep. 17, 1998.

(51) Int. Cl.[7] .................. C07H 21/04; C07H 21/02; C12Q 1/68
(52) U.S. Cl. .................. 536/23.1; 435/6; 435/91.1; 435/468; 536/23.6
(58) Field of Search .................. 435/6, 91.1, 468; 536/23.1, 23.6

(56) References Cited

FOREIGN PATENT DOCUMENTS

| WO | WO 95/19443 | 7/1995 |
| WO | WO 97/47756 | 12/1997 |
| WO | WO 98/06860 | 2/1998 |

OTHER PUBLICATIONS

Wayne A. Snedden et al., Characterization of the plant homologue of prohibitin, a gene associated with antiproliferative activity in mammalian cells, Plant Molecular Biology 33: pp. 753–756.*
Snedden et al. (1997) "Characterization of the Plant Homologue of Prohibitin, A Gene Associated With Antiproliferative Activity in Mammalian Cells" *Plant Molecular Biology* 33:753–756.
Sato et al. (1992) "The Human Prohibition Gene Located on Chromosome 17q21 Is Mutated In Sporadic Breast Cancer", *Cancer Research* 52:1643–1646.
Nuell et al. (1991) "Prohibitin, An Evolutionarily Conserved Intracellular Protein That Blocks DNA Synthesis In Normal Fibroblasts and HeLa Cells", *Molecular and Cellular Biology* 11(3):1372–1381.
Snedden et al. (Mar. 1997) "Characterization of the Plant Homologue ofProhibitin, a Gene Associated with Antiproliferative Activity in Mammalian Cells", *Plant Molecular Biology* 33(4):753–756, XP002131779.
Snedden et al. (Jun. 3, 1997) "Characterization of the Plant Homologue ofProhibitin, a Gene Associated with Antiproliferative Activity in Mammalian Cells", Database EMPLIN 'Online!, EMBL,Heidelberg, Germany, AC: U69154, ID: ATU69154, XP002131780, Abstract.
Snedden et al. (Jun. 3, 1997), "Characterization of the Plant Homologue ofProhibitin, A Gene Associated with Antiproliferative Activity in Mammalian Cells", Database EMPLIN 'Online!, EMBL,Heidelberg, Germany, AC: U69155, ID: ATU 69155, XP002131781, Abstract.
Sun et al. (Jun. 1, 1998) "Arabidopsis Genes Encoding Prohibitin: Importance for Early Development", Database TREMBL 'Online!, EMBL,Heidelberg, Germany, AC/ID 049460, XP002131782, Abstract.
Raventos et al. (1995) "A 20bp cis–acting Element is Both Necessary and Sufficient to Mediate Elicitor Response of a Maize PRms Gene", *The Plant Journal* 7(1):147–155, XP002107426.
Bushnell et al. (Jun. 1998) "Gene Engineering of Disease Resistance in Cereals", *Canadian Journal of Plant Pathology* 20(2):137–220.
Walbot (Aug. 10, 1999) "MaizeESTs From Various cDNA Libraries Sequenced at Stanford University", Database EMEST14 'Online!, EMBL,Heidelberg, Germany, AC/ID: A1944095, Xp002131783, Abstract.
Walbot (Jul. 22, 1999) "Maize ESTs From Various cDNA Libraries Sequenced at Stanford University", Database EMEST14 'Online!, EMBL,Heidelberg, Germany, AC/ID: A1854919, XP002131784, Abstract.
Walbot (Jun. 9, 1999) "MaizeESTs From Various cDNA Libraries Sequenced at Stanford University", Database EMEST12 'Online!, EMBL,Heidelberg, Germany,AC/ID: A1711810, XP002131785, Abstract.
PCT Notification of Transmittal of the International Search Report or the Declaration, mailed Mar. 15, 2000, International Application No. PCT/US99/21385, International Filing Date Sep. 15, 1999.

* cited by examiner

*Primary Examiner*—Andrew Wang
*Assistant Examiner*—Karen Lacourciere
(74) *Attorney, Agent, or Firm*—Alston & Bird LLP

(57) ABSTRACT

Compositions and methods for modulating cell cycle and cell proliferation are provided. Additionally the compositions find use in enhancing disease resistance and increasing transformation efficiency in plants. The method involves transforming a plant with a sense or antisense prohibitin sequence. The prohibitin sequence acts to regulate cell division in the plant cell. Transformed plants, plant cells, tissues, and seed are also provided having enhanced disease resistance.

24 Claims, 2 Drawing Sheets

PLANT PROHIBITION GENES AND THEIR USE

CROSS-REFERENCE TO RELATED APPLICATION

This application claims the benefit of U.S. Provisional Application No. 60/100,691 filed Sep. 17, 1998.

FIELD OF THE INVENTION

The invention relates to the genetic manipulation of plants, particularly to transforming plants with genes that regulate cell cycle, cell proliferation and enhance disease resistance.

BACKGROUND OF THE INVENTION

Prohibitin is an intracellular protein of about 280 amino acids. The protein was first discovered in mammalian cells during studies of cell senescence. The mammalian gene has been cloned and is associated with antiproliferative activity based on the capacity of microinjected prohibitin mRNA to inhibit cell cycle progression in human diploid fibroblasts.

The rat prohibitin gene was isolated for its ability to negatively regulate cell proliferation. The gene was isolated from mRNAs that were more frequently expressed in normal liver than in regenerating liver and thus was considered as a candidate for one of the tumor suppressor genes associated with breast and ovarian cancer. Prohibitin was also found to share substantial homology with the product of the Drosophila Cc gene, which encodes a protein of unknown function required for the larval to pupal transition in the fruit fly. Prohibitins are also implicated in controlling senescence and aging, with which there may be a functional link to their antiproliferative function and cell cycle control.

The prohibitin gene appears to be evolutionarily conserved. The 30 kD protein has been associated with antiproliferative activity based on the capacity of microinjected prohibitin mRNA to inhibit cell cycle progression in human diploid fibroblast-like cells. A role has been suggested for prohibitin in cell cycle regulation, replicative senescence, cellular immortalization, and the development of sporadic breast tumors. The gene is expressed in a wide variety of tissues and organisms. Prohibitin has been identified as a gene that is expressed in resting but not in dividing cells.

Disease in plants is caused by biotic and abiotic causes. Biotic causes include fungi, viruses, bacteria, and nematodes. Of these, fungi are the most frequent causative agent of disease on plants. Abiotic causes of disease in plants include extremes of temperature, water, oxygen, soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism.

As noted, among the causative agents of infectious disease of crop plants, the phytopathogenic fungi play the dominant role. Phytopathogenic fungi cause devastating epidemics, as well as causing significant annual crop yield losses. All of the approximately 300,000 species of flowering plants are attacked by pathogenic fungi. However, a single plant species can be host to only a few fungal species, and similarly, most fungi usually have a limited host range.

Plant disease outbreaks have resulted in catastrophic crop failures that have triggered famines and caused major social change. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Accordingly, molecular methods are needed to supplement traditional breeding methods to protect plants from pathogen attack. Additionally, methods are needed to control cell division and proliferation in plants.

SUMMARY OF THE INVENTION

Compositions and methods for altering cell cycle processes and cell proliferation are provided. The compositions comprise plant nucleotide sequences and proteins useful for manipulation, differentiation, development and cellular division. The sequences find use in methods for the manipulation of cell growth, both positively and negatively.

In one embodiment, the nucleotide and amino acid sequences of the invention may find use in enhancing plant culture methods and transformation. The sequences may additionally find use in methods for the activation of the plant pathogen defense system. That is, the compositions and methods of the invention can be used for enhancing resistance to plant pests. The method involves stably transforming a plant with a gene capable of inducing the plant pathogen defense system operably linked with a promoter capable of driving expression of a gene in a plant cell.

It is recognized that a variety of promoters will be useful in the invention, the choice of which will depend in part upon the desired level of expression of the disclosed genes. It is recognized that the levels of expression can be controlled to induce the disease resistance pathway resulting in levels of immunity in the plant which impart resistance in the plant to the pathogen or to induce cell death. The methods of the invention find use in controlling plant pests, including fungal pathogens, viruses, nematodes, insects, and the like.

Transformed plants and seeds, as well as methods for making such plants and seeds are additionally provided.

DETAILED DESCRIPTION OF THE INVENTION

Figure 1:
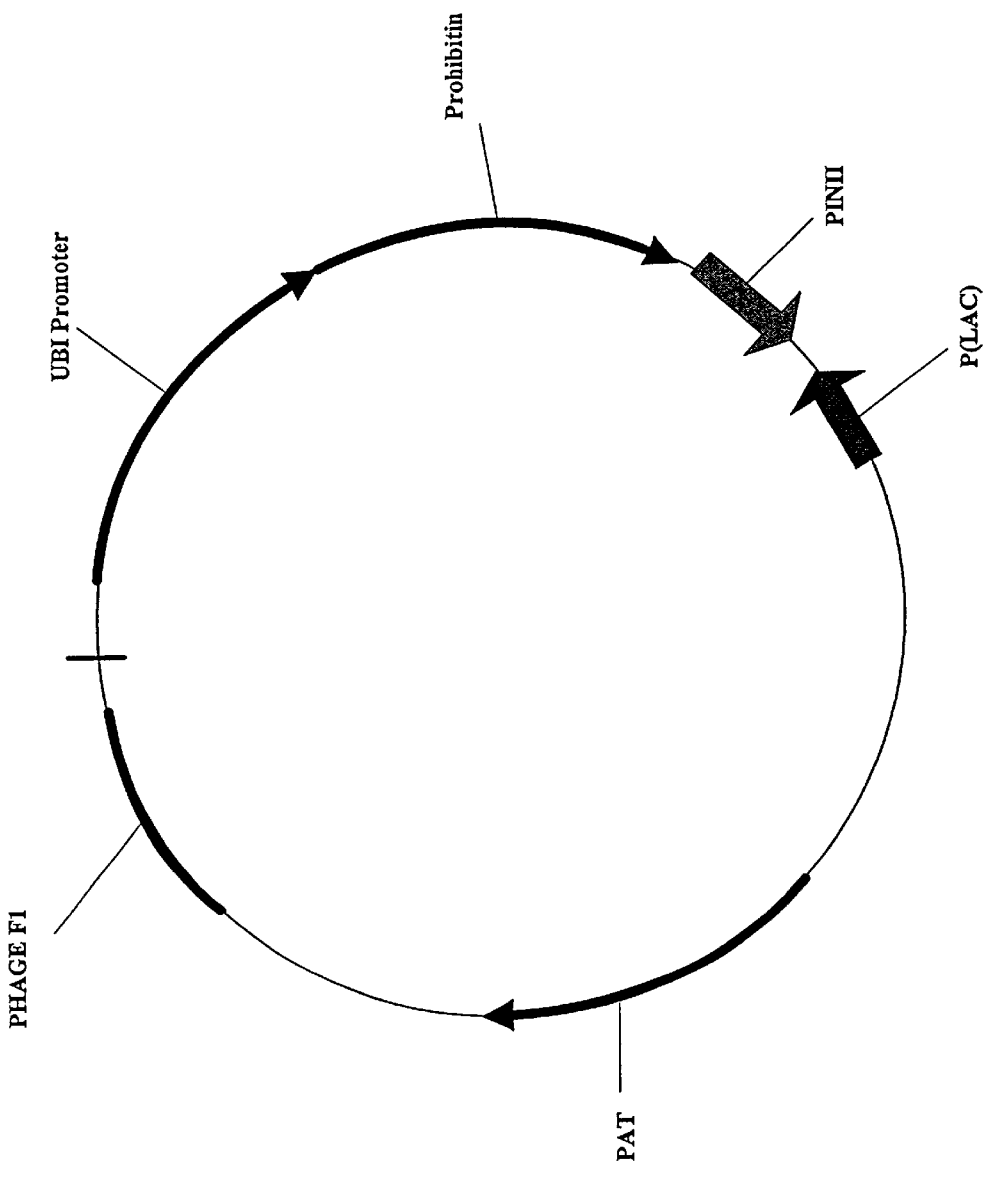
FIG. 1 schematically illustrates the plasmid construct comprising the ubiquitin promoter and a prohibitin sequence.

Compositions of the invention include prohibitins that are involved in a variety of biological processes including, controlling cell cycle, cell proliferation, tumor suppression, senescence, aging, and possibly resistance to plant disease. In particular, the present invention provides for isolated nucleic acid molecules comprising nucleotide sequences encoding the amino acid sequences shown in SEQ ID NOS: 2, 4, 6, and 8, or the nucleotide sequences encoding the DNA sequences deposited in a bacterial host as Patent Deposit Nos. 98867, 98868, 98869, and 98870, respectfully. Further provided are polypeptides having an amino acid sequence encoded by a nucleic acid molecule described herein, for example those set forth in SEQ ID NOS: 1, 3, 5, and 7 deposited in a bacterial host as Patent Deposit Nos. 98867, 98868, 98869, and 98870, respectively and fragments and variants thereof.

Plasmids containing the nucleotide sequences of the invention were deposited with the Patent Depository of the American Type Culture Collection (ATCC), 10801 University Boulevard, Manassas, Va., 20110–2209 and assigned Patent Deposit Nos. 98867, 98868, 98869, and 98870. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence retain prohibitin-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a prohibitin nucleotide sequence that encodes a biologically active portion of a prohibitin protein of the invention will encode at least 15, 25, 30, 50, 100, 150, 200, or 250 contiguous amino acids, or up to the total number of amino acids present in a full-length prohibitin protein of the invention (for example, 289, 284, 282, 289 amino acids for SEQ ID NO: 2, 4, 6, and 8 respectively). Fragments of a prohibitin nucleotide sequence that are useful as hybridization probes for PCR primers generally need not encode a biologically active portion of a prohibitin protein.

Thus, a fragment of a prohibitin nucleotide sequence may encode a biologically active portion of a prohibitin protein, or it may be a fragment that can be used as a hybridization probe or PCR primer using methods disclosed below. A biologically active portion of a prohibitin protein can be prepared by isolating a portion of one of the prohibitin nucleotide sequences of the invention, expressing the encoded portion of the prohibitin protein (e.g., by recombinant expression in vitro), and assessing the activity of the encoded portion of the prohibitin protein. Nucleic acid molecules that are fragments of a prohibitin nucleotide sequence comprise at least 16, 20, 50, 75, 100, 150, 200, 250, 300, 350, 400, 450, 500, 550, 600, 650, 700, 800, 900, 1,000, 1,100 nucleotides, or up to the number of nucleotides present in a full-length prohibitin nucleotide sequence disclosed herein (for example, 1323, 1162, 1133, and 1148 nucleotides for SEQ ID NOS: 1, 3, 5, and 7 respectively).

By "variants" is intended substantially similar sequences. For nucleotide sequences, conservative variants include those sequences that, because of the degeneracy of the genetic code, encode the amino acid sequence of one of the prohibitin polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a prohibitn protein of the invention. Generally, variants of a particular nucleotide sequence of the invention will have at least 40%, 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein, or substitution of one or more amino acids at one or more sites in the native protein. Variant proteins encompassed by the present invention are biologically active, that is they continue to possess the desired biological activity of the native protein, that is, prohibitin-like activity as described herein. Such variants may result from, for example, genetic polymorphism or from human manipulation. Biologically active variants of a native prohibitin protein of the invention will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the prohibitin proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof Such variants will continue to possess the desired prohibitin-like activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by the induction of the plant defense system. See, for example U.S. Pat. No. 5,614,395, herein incorporated by reference. Additionally, the activity can also be evaluated by a decrease in cell division rate. This decrease in division rate is reflected in larger cell size, less rapid incorporation of radiolabeled nucleotides and slower growth. See for example, Nuell, M. J. et al. (1991) *Molecular and Cellular Biology* 11:1372–1381, and Roskams, J. A. e[009f] al. (1993) *Journal of Cellular Physiology* 157:289–295.

Variant nucleotide sequences and proteins also encompass sequences and proteins derived from a mutagenic and recombinogenic procedure such as DNA shuffling. With such a procedure, one or more different prohibitin coding sequences can be manipulated to create a new prohibitin possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the prohibitin gene of the invention and other known prohibitin genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1 994) *Nature* 370:389–391; Crameri et al. (1997) *Nature Biotech.* 15:436–438; Moore et al. (1997) *J. Mol. Biol.* 272:336–347; Zhang et al (1997) *Proc. Natl. Acad Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire prohibitin sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the prohibitin sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire prohibitin sequence disclosed herein, or one or more portions thereof, may be used as a probe capable of specifically hybridizing to corresponding prohibitin sequences and messenger RNAs. To achieve specific hybridization under a variety of conditions, such probes include sequences that are unique among prohibitin sequences and are preferably at least about 10 nucleotides in length, and most preferably at least about 20 nucleotides in length. Such probes may be used to amplify corresponding prohibitin sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for a prohibitin protein and which hybridize to the prohibitin sequences disclosed herein, or to fragments thereof, are encompassed by the present invention. Such sequences will be at least 40% to 50% homologous, about 60% to 70% homologous, and even about 80%, 85%, 90%, 95% to 98% homologous or more with the disclosed sequences. That is, the sequence identity of sequences may range, sharing at least about 40% to 50%, about 60% to 70%, and even about 80%, 85%, 90%, 95% to 98% sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman et al. (1970) *J. Mol. Biol.* 48:443; the search-for-similarity-method of Pearson et al. (1988) *Proc. Natl. Acad. Sci.* 85:2444; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Nucleotide and amino acid sequences for plant prohibitins are provided. The sequences find use in controlling cell cycle, cell proliferation, tumor suppression, senescence, aging, and development. Expression of the sequences in the cell negatively controls cell cycle in the early G1 phase and inhibits DNA synthesis. In like manner, prohibitin antisense oligonucleotides can be used to block prohibitin expression and promote cell cycle through S-phase.

The prohibitin protein is localized in the mitochondria, especially in the inner mitochondria membrane and near the periphery. Since mitochondrial inner membrane proteins often control ion transport and ATP production, prohibitin may be involved in these processes, particularly, in mitochondrial calcium efflux which regulates ATP formation. Thus, the sequences of the invention additionally find use in manipulating differentiation, development and cellular division. The sequences are useful in methods for the manipulation of cell growth both positively and negatively.

The prohibitin sequences of the invention form part of a structurally-related family of proteins. (See Experimental section, Example 11). Stomatins and HR-inducing (hypersensitive response-inducing) genes are also members of this family. See U.S. Patent Application entitled "Maize Stomatin Genes and Methods of Use" filed concurrrently herewith and U.S. patent application Ser. No. 09/256,158 filed on Feb. 24, 1999, entitled, "Genes for Activation of Plant Pathogen Defense Systems."

Sequence analysis has further indicated that the prohibitin sequences of the invention are related to a tobacco cDNA that causes lesions similar to hypersensitive response lesions in plant-pathogen interactions, and to an Arabidopsis cDNA associated with systemic acquired resistance to pathogens. Thus, the compositions of the invention may find use in methods for protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

The nucleotide sequences of the invention include those which are involved in activating plant systems for defense against pathogens. The gene products, generally proteins or polypeptides, function to activate the defense system. The activation of the defense system may involve inducing resistance of the plant to pathogen invasion or alternatively, the gene products may turn on the hypersensitive response in the plant. The hypersensitive response is a localized lesion of necrotic tissue that forms around the site of pathogen infection. This plant-induced necrosis thwarts progression of the disease by depriving the pathogen of plant material for its consumption.

Alternatively, activation of the plant defense system may involve the induced production of gene products, such as PR proteins and various secondary metabolites, many of which are antipathogenic. The induction may involve inducing the accumulation of cytotoxic phytoalexins, the deposition of callose and lignin in cell walls. Likewise, the induction may involve the activation of transcription factors, reactive oxygen species, ion fluxes, G proteins, salicylic acids and other HR and plant defense regulators. It is recognized that the present invention is not dependent upon a particular mechanism of defense. Rather, the genes and methods of the invention work to increase resistance of the plant to pathogens independent of how that resistance is brought.

As discussed, the expression of the prohibitin molecules in the plant cell may induce the disease resistance pathway or induces immunity, i.e. disease resistance, in the plant. That is, the expression of the genes may induce a defense response in the cell or may turn on the disease resistance pathway to obtain cell death. The end result can be controlled by the level of expression of the prohibitin sequences in the plant. Where the expression is sufficient to cause cell death, such response is a receptor-mediated programmed response. See, for example, Ryerson and Heath (1996) *Plant Cell* 8:393–402 and Dangl et al. (1996) *Plant Cell* 8:1793–1807.

The prohibitin molecules described herein may be used alone or in combination with other proteins or agents or methods available in the art for enhancing disease and pathogens and pathogen resistance in plants. Other plant defense proteins include those described in U.S. patent application Ser. No. 09/256,898 entitled "Methods for Enhancing Disease Resistance in Plants" filed on Feb. 24, 1999.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus; *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Clavicepspurpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophominaphaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillusflavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Cur-* vularia inaequalis, Curvularia pallescens, Clavibacter michiganense subsp. nebraskense, Trichoderma viride, Maize Dwarf Mosaic Virus A & B, Wheat Streak Mosaic Virus, Maize Chlorotic Dwarf Virus, Claviceps sorghi, Pseudonomas avenae, Erwinia chrysanthemi pv. zea, Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: Exserohilum turcicum, Colletotrichum graminicola (Glomerella graminicola), Cercospora sorghi, Gloeocercospora sorghi, Ascochyta sorghina, Pseudomonas syringae p.v. syringae, Xanthomonas campestris p.v. holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi, Sugarcane mosaic H, Maize Dwarf Mosaic Virus A & B, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola, etc.

Nematodes include parasitic nematodes such as root-knot, cyst, and lesion nematodes, including Heterodera and Globodera spp; particularly Globodera rostochiensis and globodera pailida (potato cyst nematodes); Heterodera glycines (soybean cyst nematode); Heterodera schachtii (beet cyst nematode); and Heterodera avenae (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: Ostrinia nubilalis, European corn borer; Agrotis ipsilon, black cutworm; Helicoverpa zea, corn earworm; Spodoptera frugiperda, fall armyworm; Diatraea grandiosella, southwestern corn borer; Elasmopalpus lignosellus, lesser cornstalk borer; Diatraea saccharalis, surgarcane borer; Diabrotica virgifera, western corn rootworm; Diabrotica longicornis barberi, northern corn rootworm; Diabrotica undecimpunctata howardi, southern corn rootworm; Melanotus spp., wireworms; Cyclocephala borealis, northern masked chafer (white grub); Cyclocephala immaculata, southern masked chafer (white grub); Popillia japonica, Japanese beetle; Chaetocnema pulicaria, corn flea beetle; Sphenophorus maidis, maize billbug; Rhopalosiphum maidis, corn leaf aphid; Anuraphis maidiradicis, corn root aphid; Blissus leucopterus leucopterus, chinch bug; Melanoplus femurrubrum, redlegged grasshopper; Melanoplus sanguinipes, migratory grasshopper; Hylemya platura, seedcorn maggot; Agromyza parvicornis, corn blot leafminer; Anaphothrips obscrurus, grass thrips; Solenopsis milesta, thief ant; Tetranychus urticae, twospotted spider mite; Sorghum: Chilo partellus, sorghum borer; Spodoptera frugiperda, fall armyworm; Helicoverpa zea, corn earworm; Elasmopalpus lignosellus, lesser cornstalk borer; Feltia subterranea, granulate cutworm; Phyllophaga crinita, white grub; Eleodes, Conoderus, and Aeolus spp., wireworms; Oulema melanopus, cereal leaf beetle; Chaetocnema pulicaria, corn flea beetle; Sphenophorus maidis, maize billbug; Rhopalosiphum maidis; corn leaf aphid; Sipha flava, yellow sugarcane aphid; Blissus leucopterus leucopterus, chinch bug; Contarinia sorghicola, sorghum midge; Tetranychus cinnabarinus, carmine spider mite; Tetranychus urticae, twospotted spider mite; Wheat: Pseudaletia unipunctata, army worm; Spodoptera frugiperda, fall armyworm; Elasmopalpus lignosellus, lesser cornstalk borer; Agrotis orthogonia, western cutworm; Elasmopalpus lignosellus, lesser cornstalk borer; Oulema melanopus, cereal leaf beetle; Hypera punctata, clover leaf weevil; Diabrotica undecimpunctata howardi, southern corn rootworm; Russian wheat aphid; Schizaphis graminum, greenbug; Macrosiphum avenae, English grain aphid; Melanoplus femurrubrum, redlegged grasshopper; Melanoplus differentialis, differential grasshopper; Melanoplus sanguinipes, migratory grasshopper; Mayetiola destructor, Hessian fly; Sitodiplosis mosellana, wheat midge; Meromyza americana, wheat stem maggot; Hylemya coarctata, wheat bulb fly; Frankliniella fusca, tobacco thrips; Cephus cinctus, wheat stem sawfly; Aceria tulipae, wheat curl mite; Sunflower: Suleima helianthana, sunflower bud moth; Homoeosoma electellum, sunflower moth; zygogramma exclamationis, sunflower beetle; Bothyrus gibbosus, carrot beetle; Neolasioptera murtfeldtiana, sunflower seed midge; Cotton: Heliothis virescens, cotton budworm; Helicoverpa zea, cotton bollworm; Spodoptera exigua, beet armyworm; Pectinophora gossypiella, pink bollworm; Anthonomus grandis grandis, boll weevil; Aphis gossypii, cotton aphid; Pseudatomoscelis seriatus, cotton fleahopper; Trialeurodes abutilonea, bandedwinged whitefly; Lygus lineolaris, tarnished plant bug; Melanoplus femurrubrum, redlegged grasshopper; Melanoplus differentialis, differential grasshopper; Thrips tabaci, onion thrips; Franklinkiella fusca, tobacco thrips; Tetranychus cinnabarinus, carmine spider mite; Tetranychus urticae, twospotted spider mite; Rice: Diatraea saccharalis, sugarcane borer; Spodoptera frugiperda, fall armyworm; Helicoverpa zea, corn earworm; Colaspis brunnea, grape colaspis; Lissorhoptrus oryzophilus, rice water weevil; Sitophilus oryzae, rice weevil; Nephotettix nigropictus, rice leafhopper; Blissus leucopterus leucopterus, chinch bug; Acrosternum hilare, green stink bug; Soybean: Pseudoplusia includens, soybean looper; Anticarsia gemmatalis, velvetbean caterpillar; Plathypena scabra, green cloverworm; Ostrinia nubilalis, European corn borer; Agrotis ipsilon, black cutworm; Spodoptera exigua, beet armyworm; Heliothis virescens, cotton budworm; Helicoverpa zea, cotton bollworm; Epilachna varivestis, Mexican bean beetle; Myzus persicae, green peach aphid; Empoasca fabae, potato leafhopper; Acrosternum hilare, green stink bug; Melanoplus femurrubrum, redlegged grasshopper; Melanoplus differentialis, differential grasshopper; Hylemya platura, seedcorn maggot; Sericothrips variabilis, soybean thrips; Thrips tabaci, onion thrips; Tetranychus turkestani, strawberry spider mite; Tetranychus urticae, twospotted spider mite; Barley: Ostrinia nubilalis, European corn borer; Agrotis ipsilon, black cutworm; Schizaphis graminum, greenbug; Blissus leucopterus leucopterus, chinch bug; Acrosternum hilare, green stink bug; Euschistus servus, brown stink bug; Delia platura, seedcorn maggot; Mayetiola destructor, Hessian fly; Petrobia latens, brown wheat mite; Oil Seed Rape: Brevicoryne

*brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

The prohibitin sequences of the invention may induce cell death and thus it is recognized that the sequences may find use in applications of male and/or female sterility.

As noted above, the sequences of the invention may find use in regulating or modulating cell cycle. That is, the sequences can be used to block or reduce cell cycle arrest. Thus, the sequences may be used to increase transformation efficiency, particularly in plant cells. Transformation efficiency is often limited by cell proliferation during and following uptake of the introduced DNA. Upon uptake of introduced DNA, the cell cycle often is arrested, decreasing transformation events as it is believed that the integration of foreign DNA occurs in dividing cells. The delivery of damaged DNA such as that introduced by particle bombardment induces an immediate cell cycle arrest. This inhibition may be avoided by ectopic transient overexpression or down-regulation of genes that regulate cell division.

Besides increasing transformation efficiency in plants, the methods find use in transforming genotypes of plant species recalcitrant to transformation. Generally, all methods of plant transformation yield low transformation frequency. Thus, the methods of the invention can be used with any transformation method including Agrobacterium infection, electroporation, protoplast fusion, particle bombardment, and the like.

As prohibitins are generally thought to inhibit cell cycle and/or cell proliferation, to increase cell division, inhibition of prohibitin is desired. This increase in cell division may be brought about by expression of the prohibitin sequence or interference with the prohibitin gene product. Any method for suppression of expression can be used in the invention. Such methods are known in the art and include antisense constructions, cosuppression, protein and mRNA manipulation, use of nucleotide or ribonucleotide sequences, antibodies, proteins, peptides, and the like. Over-expression of the prohibitin sequence may lead to co-suppression. Antisense sequences may be used to down regulate expression. Antibodies or proteins may be used to transiently disrupt the growth inhibitory properties of prohibitin. Likewise, contransformation with ribo- or deoxyribo-oligonucleotides based on prohibitin sequences may be used to down-regulate expression.

The delivery of nucleotides, proteins and antibodies can be accomplished by indirect methods such as Agrobacterium or alternatively by direct methods such as electroporation, particle bombardment or sonication.

In methods to increase transformation efficiency, prohibitin expression can be manipulated during and immediately following the introduction of the nucleotide sequences to be integrated into the plant genome. However, to avoid tumorous or uncontrolled growth, the alteration of cell division will need to be limited. To avoid problems associated with ectopic stable expression of the sequences of the invention, strategies for transient expression of the sequences may be needed. In this manner, as noted above, delivery of peptides, DNA, RNA, or antibodies could be used to enhance transgene integration by transient stimulation of cell division. For example, inactivation of Rb or prohibitin protein with antibodies or antisense RNA would work to drive cells into S-phase.

By "increasing transformation efficiency" is intended that the number of transformed plants obtained from a single transformation event is increased at least 1, 2, 3 fold to 10 fold or more.

The sequences and methods of the invention also find use in initiating tissue cultures in plant genotypes recalcitrant to culturing and/or transformation. Cell division rates in maize and other plants affect both the culture initiation frequencies and transformation frequencies of the plant. In some genotypes it is extremely difficult to stimulate cell proliferation in vitro. This lack of adequate culture response has a negative effect on transformation as cell culture is required for most transformation methods. Thus, methods of the invention can be used to stimulate cell division and initiate plant tissue cultures.

The methods find use in initiating cell cultures or increasing transformation in any plant of interest. Plants of interest include, but are not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably plants include corn, soybean, sunflower, safflower, Brassica, wheat, barley, rye, alfalfa, and sorghum.

The present invention also provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a prohibitin gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The prohibitin genes of the invention can be introduced into any plant. The genes to be introduced can be conveniently used in expression cassettes for introduction and expression in any plant of interest. Such expression cassettes will comprise a transcriptional initiation region linked to the prohibitin sequence of interest. Such an expression cassette is provided with a plurality of restriction sites for insertion of the gene of interest to be under the transcriptional regulation of the regulatory regions. The expression cassette may additionally contain selectable marker genes.

The transcriptional initiation region, the promoter, may be native or analogous or foreign or heterologous to the plant host or to the coding sequence. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

While it may be preferable to express the sequences using heterologous promoters, the native promoter may be used. Such constructs would change expression levels of prohibitins in the plant or plant cell. Thus the phenotype of the plant or plant cell is altered.

The expression cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of A. tumefaciens, such as the octopine synthase and nopaline synthase termination regions. See also, Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell 2:1261–1272; Munroe et al. (1990) Gene 91:151–158; Ballas et al. (1989) Nucleic Acids Res. 17:7891–7903; Joshi et al. (1987) Nucleic Acid Res. 15:9627–9639.

The genes of the invention are provided in expression cassettes for expression in the plant of interest. The cassette will include 5' and 3' regulatory sequences operably linked to the gene of interest. The cassette may additionally contain at least one additional gene to be cotransformed into the organism. Alternatively, the additional gene(s) can be provided on another expression cassette. Where appropriate, the gene(s) may be optimized for increased expression in the transformed plant. That is, the genes can be synthesized using plant preferred codons for improved expression. See, for example, Campbell and Gowri (1990) Plant Physiol. 92:1–11 for a discussion of host-preferred codon usage. Methods are available in the art for synthesizing plant preferred genes. See, for example, U.S. Pat. Nos. 5,380,831, 5,436,391, and Murray et al. (1989) Nucleic Acids Res. 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) PNAS USA 86:6126–6130); potyvirus leaders, for example, TEV leader (Tobacco Etch Virus) (Allison et al. (1986); MDMV leader (Maize Dwarf Mosaic Virus); Virology 154:9–20), and human immunoglobulin heavy-chain binding protein (BiP), (Macejak, D. G., and P. Sarnow (1991) *Nature* 353:90–94; untranslated leader from the coat protein mRNA of alfalfa mosaic virus (AMV RNA 4), (Jobling, USA, and Gehrke, L., (1987) *Nature* 325:622–625; tobacco mosaic virus leader (TMV), (Gallie, D. R. et al. (1989) *Molecular Biology of RNA*, pages 237–256; and maize chlorotic mottle virus leader (MCMV) (Lommel, USA et al. (1991) *Virology* 81:382–385). See also, Della-Cioppa et al (1987) *Plant Physiology* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

It is recognized that the prohibitin sequences of the invention may be used to generate antisense constructions that are complementary to at least a portion of the messenger RNA (mRNA) for the prohibitin sequences. As used herein, "antisense orientation" includes reference to a duplex polynucleotide sequence which is operably linked to a promoter in an orientation where the antisense strand is transcribed. The DNA construct is then transformed into plants and the antisense strand of RNA is produced. It is appreciated that control of gene expression in either sense or anti-sense orientation may have a direct impact on the observable plant characteristics.

Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

While novel nucleotide sequences are disclosed, it is recognized that sequences from other sources, including mammalian sources, may be used in the practice of the invention. Such nonplant sequences can be constructed using plant preferred codons, if necessary, for expression in plants. Additionally, promoters capable of driving expression of the sequences can be used with such sequences.

A number of promoters can be used in the practice of the invention. The promoters can be selected based on the desired outcome. When the genes are expressed at levels to causes cell death, an inducible promoter or tissue-preferred can be used to drive the expression of the genes of the invention. The inducible promoter must be tightly regulated to prevent unnecessary cell death yet be expressed in the presence of a pathogen to prevent infection and disease symptoms. Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116. See, also U.S. patent application Ser. No. 09/257,584, entitled "Constitutive Maize Promoters" filed on Feb. 25, 1999 herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang, Y (1996) *Proc. Natl. Acad. Sci. USA* 93: 14972–14977. See also, Chen et al. (1996) *Plant J.* 10:955–966; Zhang and Sing (1994) *Proc. Natl. Acad Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiological and Molecular Plant Pathology* 41:189–200).

Additionally, as pathogens find entry into plants through wounds or insect damage, a wound inducible promoter may be used in the constructions of the invention. Such wound inducible promoters include potato proteinase inhibitor (pin II) gene (Ryan, C., *Annu Rev Phytopath* 28:425–449; Duan et al. *Nature Biotechnology* 14:494–498); wun1 and wun2, U.S. Pat. No. 5,428,148; win1 and win2 (Stanford et al. *Mol Gen Genet* 215:200–208); systemin (McGurl et al. *Science* 225:1570–1573); WIP1 (Rohmeier et al. *Plant Mol Biol* 22:783–792; Eckelkamp et al. *FEBS Letters* 323:73–76); MPI gene (Corderok et al. *The Plant Journal* 6(2): 141–150); and the like, herein incorporated by reference.

Where low level expression is desired, weak promoters will be used. It is recognized that weak inducible promoters may be used. Additionally, either a weak constitutive or a weak tissue-preferred promoter may be used. Such weak promoters cause activation of the plant defense system short of hypersensitive cell death. Thus, there is an activation of the plant defense system at levels sufficient to protect from pathogen invasion. In this state, there is at least a partial activation of the plant defense system wherein the plant produces increased levels of antipathogenic factors such as PR proteins, i.e., PR1, chitinases, β-glucanases, etc.; secondary metabolites; phytoalexins; reactive oxygen species; and the like.

Generally, by "weak promoter" is intended either a promoter that drives expression of a coding sequence at a low level. By low level is intended at levels of about 1/1000 transcripts per cell to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 (PCT Application Serial No. U.S.99/03863), the core 35S promoter, and the like. Other constitutive promoters include, for example, U. S. Pat. Nos. 5,608,149; 5,608,144; 5,604,121; 5,569,597; 5,466,785; 5,399,680; 5,268,463; 5,608,142. See also, copending application entitled "Constitution Maize Promoters" U.S. application Ser. No. 50/076,075, herein incorporated by reference.

Tissue-preferred promoters include Yamamoto et al. (1997) *Plant J.* 12(2):255–265; Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl Cell Differ.* 20:181–196; Orozco et al. (1993) *Plant Mol Biol.* 23(6):1129–1138; Matsuoka et al. (1993) *Proc Natl Acad Sci USA* 90(20):9586–9590; and Guevara-Garcia et al. (1993) *Plant J.* 4(3):495–505. Such promoters can be modified, if necessary, for weak expression.

The genes of the present invention can be used to transform any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago saliva*), rice (*Oryza saliva*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Generally, methods for antibody production are known in the art. The antibodies of the invention selectively bind to the prohibitin protein and its variants and fragments. An antibody is considered to selectively bind, even if it also binds to other proteins that are not substantially homologous with the prohibitin protein. These other proteins share homology with a fragment or domain of the prohibitin protein. This conservation in specific regions gives rise to antibodies that bind to both proteins by virtue of the homologous sequence. In this case, it would be understood that antibody binding to the prohibitin protein is still selective.

Antibodies can be polyclonal, or more preferably, monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$U.S. or $^{3}$H.

To generate antibodies, an isolated receptor polypeptide is used as an immunogen to generate antibodies using standard techniques for polyclonal and monoclonal antibody preparation. Either the full-length protein or antigenic peptide fragment can be used. Preferably, the antigenic peptide comprises at least 10 amino acid residues, more preferably at least 15 amino acid residues, even more preferably at least 20 amino acid residues, and most preferably at least 30 amino acid residues. An appropriate immunogenic preparation can be derived from native, recombinantly expressed, protein or chemically synthesized peptides.

The following examples are offered by way of illustration and not by way of limitation.

EXPERIMENTAL

Example 1

Disease Resistant Transient Gene Expression Assay Using Biolistics Particle Bombardment A transient gene expression assay, as modified from Nelson and Bushnell (1997) (*Transgenic Res.* 6:233–244), is used to evaluate the ability of an introduced prohibitin gene, whose expression product would induce the pathogen defense system in a host plant cell, to confer a hypersensitive response within the host cell. In the method, a particle bombardment system is used to simultaneously introduce a construct comprising a reporter gene driven by a constitutive promoter and a construct comprising a prohibitin gene with its promoter into maize cells for the purposes of studying physiological processes, foremost amongst them the plant defense response.

Figure 2:
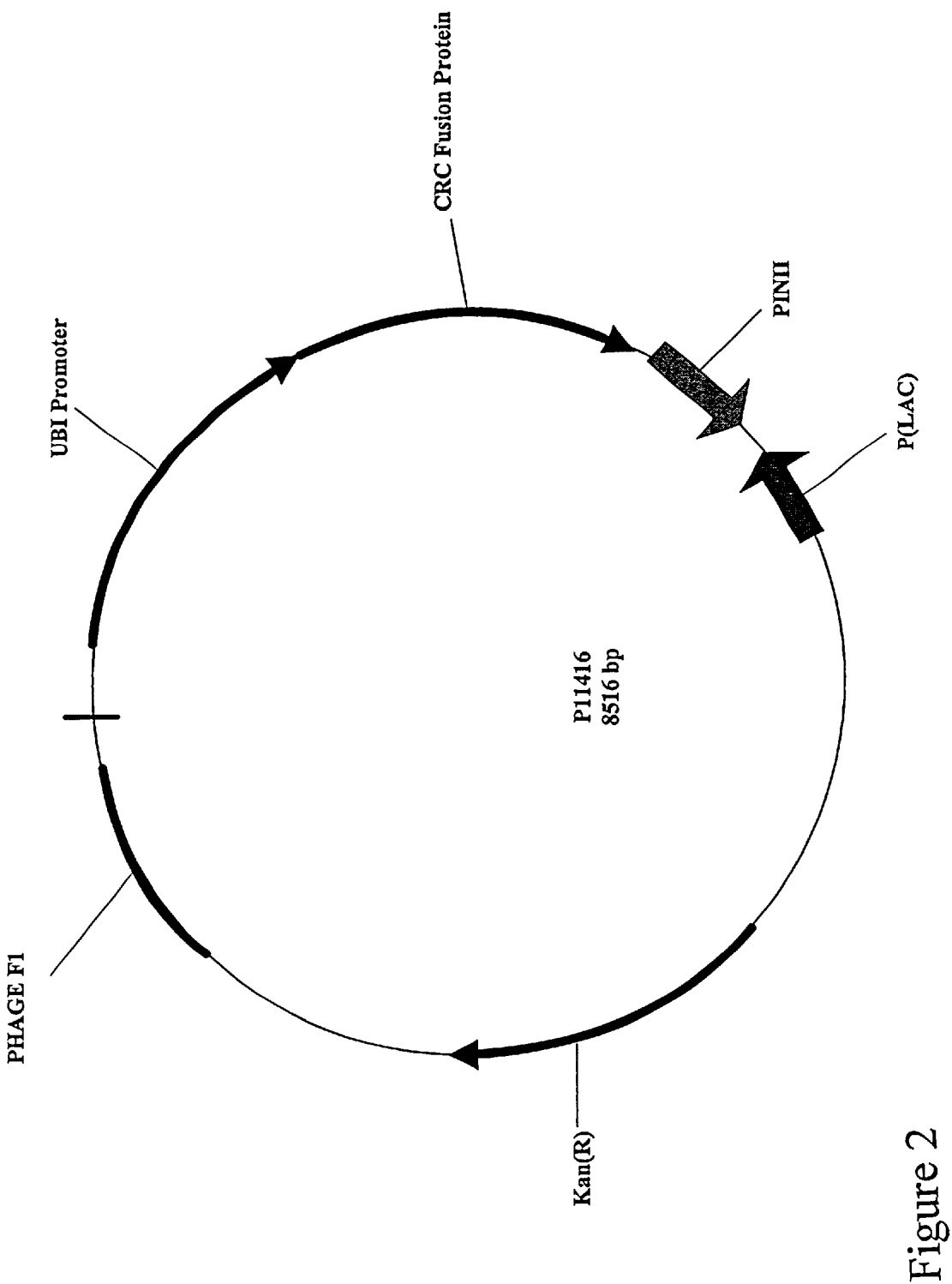
FIG. 2 schematically illustrates the plasmid construct comprising the ubiquitin promoter and CRC fusion protein gene.

In this example, the first construct comprises a ubiquitin promoter driving the expression of the reporter CRC fusion protein gene, which when expressed causes cells to turn red due to anthocyanin production (FIG. 2). Other reporter genes, such as GUS, luciferase, or green fluorescent protein, can be used in this assay. The second construct comprises one of the prohibitin genes of FIG. 1 driven by the constitutive ubiquitin promoter. The second plasmid also contains the selectable marker gene PAT (Wohlleben et al. (1988) *Gene* 70:25–37) that confers resistance to the herbicide Bialaphos. Transformation is performed as follows. All media recipes are in the Appendix.

Following cobombardment of cells with these constructs, expression of the prohibitin genes within a cell causes a hypersensitive-type disease response involving cell death, or at the very least radically redirected gene expression. Such cell death disrupts the expression of the reporter gene, such that the occurrence of visible, anthocyanin-containing phenotypes is suppressed in these cobombardment experiments.

Tissue Sources.

Experiments are performed with immature embryos, essentially the scutellar surface. Mature embryos from germinated seeds, as well as leaves have also been used with similar results.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

DNA Sources.

The DNA constructs of interest used in this example include: a plasmid (FIG. 2), comprising the ubiquitin promoter (ubi) and the CRC fusion protein gene (ubi::CRC fusion), the expression of which yields the anthocyanin-producing, or red cell, phenotype; and a plasmid comprising the ubiquitin promoter and a prohibitin sequence of the invention (ubi::prohibitin) (FIG. 1), the expression of which yields the prohibitin product. Plasmid p7770 (not shown), comprising an empty ubiquitin promoter construct (ubi::pinII terminator), is used as a control to balance promoter site molarity; and plasmid p7731 (not shown), an inert DNA filler, is used to balance the amount of DNA shot with each bombardment episode.

Preparation of DNA

The plasmid vector ubi::CRC fusion construct alone (FIG. 2) or both the ubi::CRC fusion construct (FIG. 2) and the ubi::prohibitin construct (FIG. 1) are precipitated onto 1.1 μm (average diameter) tungsten pellets using a CaCl$_2$ precipitation procedure as follows:

100 μl prepared tungsten particles in water
10 μl (1 μg) DNA in TrisEDTA buffer (1 μg total)
100 μl 2.5 M CaCl$_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Quantification and Verification of Gene Expression.

Expression of the CRC fusion gene is quantified by visual means 16 to 48 hours, more usually 36 hours, following bombardment. Cells expressing the CRC fusion protein gene are red in color.

Activation of the defense system, using the maize PR1 protein as a marker, is verified with an antibody Western blot for the PR-1 class of pathogenesis-related proteins. Forty-eight hours after bombardment, 18 embryos for each treatment are pooled and their protein extracted and run on S.O.S.-PAGE, electroblotted onto 0.2 micron PVDV membrane, and probed with antibodies raised against tobacco PR-1 protein.

Example 2

Using Prohibitin in a Two-hybrid System to Identify Maize Genes Involved in Control Of Proliferation Prohibitin gene expression plays a prominent role as an antiproliferative agent, inhibiting cell cycle progression. The protein encoded by the prohibitin gene is sequestered in the mitochondria, and appears to be a trans-acting tumor suppressor or growth regulator. Prohibitin also appears to be membrane associated, and has been implicated in calium fluxes in the cell. As such, the prohibitin genes and their encoded proteins can potentially be used to identify other proteins involved in the above processes. This can be done using the prohibitin gene as bait (the target fused to the DNA-binding domain) in a yeast two-hybrid screen. Methods for two-hybrid library construction, cloning of the reporter gene, cloning of the DNA-binding and activation domain hybrid gene cassettes, yeast culture, and transformation of the yeast are all done according to well-established methods (see Sambrook et al., 1990; Ausubel et al., 1990; Hannon and Bartels, 1995). When maize prohibitin is used as bait in such a two-hybrid screen, proteins that interact with prohibitin such as maize homologs to the mammalian BAP37 gene-product (Coates P J et al., 1997, *Current Biology* 7:R607–R610) are identified.

Example 3

Transient Prohibitin-antisense Expression Stimulates Cell Division and Enhances Transgene Integration Regardless of the method of DNA delivery, cells competent for the integration of foreign DNA must be actively dividing. There is a growing body of evidence suggesting that integration of foreign DNA occurs in dividing cells (this includes both Agrobacterium and direct DNA delivery methods). It has long been observed that dividing transformed cells represent only a fraction of cells that transiently express a transgene. It is well known (in non-plant systems) that the delivery of damaged DNA, (similar to what we introduce by particle gun delivery methods) induces checkpoint controls and inhibits cell cycle progression. Cell cycle blockage is typically regulated by tumor suppressor proteins such as prohibitin. This inhibition can be obviated by transient down-regulation of negative regulators such as prohibitin. Regardless of the mechanism of arrest; i.e. presence of damaged DNA or delivery into a non-cycling differentiated cell, stimulation of the cell cycle will increase integration frequencies.

To demonstrate this, a prohibitin-antisense sequence is cloned into a cassette with a constitutive promoter (i.e. either a strong maize promoter such as the ubiquitin promoter including the first ubiquitin intron, or a weak constitutive promoter such as nos). Delivery of the prohibitin-antisense DNA in an appropriate plant expression cassette (for example, in a UBI::ZmProhibitin-antisense::pinII-containing plasmid) along with UBI::bar::pinII can be accomplished through numerous well-established methods for plant cells, including for example particle bombardment (as described in example 1), sonication, PEG treatment or electroporation of protoplasts, electroporation of intact tissue, silica-fiber methods, microinjection or Agrobacterium-mediated transformation. Using one of the above methods, DNA is introduced into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids. Transient expression of the prohibitin-antisense down-regulates prohibitin which in turn releases the cells to progress through the cell cycle and divide. This effectively overcomes the G1/S checkpoint controls, and increases the proportion of recipient-cells (i.e. into which DNA was introduced) that enter S-phase. This stimulation through the G1/S transition in cells harboring transgenic plasmid DNA provides an optimal cellular environment for integration of the introduced genes. Cytological methods can be used to verify increased frequencies of progression through S-phase and mitosis (i.e. for cells in which a visual marker such as GFP was transformed alongside Prohibitin the green fluorescent cells will exhibit a higher mitotic index). Cells in S-phase (undergoing DNA replication) can be monitored by detecting nucleotide analog incorporation. For example, following incubation of cells with bromodeoxyuridine (BrdU) incorporation of this thymidine analog can be detected by methods such as antiBrdU immunocytochemistry or through enhancement of Topro3 fluorescence following BrdU labeling. Prohibitin expression will increase the proportion of cells incorporating BrdU (i.e. a higher percentage of transformed cells will incorporate BrdU relative to untransformed cells). Increased DNA synthesis can also be monitored using such methods as fluorescence activated cell sorting (FACS) of protoplasts (or nuclei), in conjunction with appropriate BrdU-insensitive fluorescent DNA labels such as propidium iodide and DAPI or BrdU-detecting methods described above. For example, tissue is homogenized to release nuclei that are analyzed using the FACS for both green fluorescence (from our accompanying GFP marker) and DNA content. Such FACS analysis demonstrates that expression of a co-transformed GFP reporter correlates with Prohibitin-induced changes in the ratios of cells in G1, S and G2. Similar experiments can be run using the fluorescently labeled anti-BrdU antisera to demonstrate that Prohibitin expression increased the percentage of cells in S-phase. Cell cycle stage-specific probes can also be used to monitor cell cycle progression. For example, numerous spindle-associated proteins are expressed during a fairly narrow window during mitosis, and antibodies or nucleic acid probes to cyclins, histones, or DNA synthesis enzymes can be used as positive markers for the G1/S transition. For cells that have received the Prohibitin-antisense gene cassette, stimulation of the cell cycle is manifested in an increased mitotic index, detected by staining for mitotic figures using a DNA dye such as DAPI or Hoechst 33258. FACS analysis of prohibitin-antisense-expressing cells shows that a high percentage of cells have progressed into or through S-phase. Progression through S-phase will be manifested by fewer cells in G1 and more rapid cycling times (i.e. shorter G1 and G2 stages). A higher percentage of cells are labeled when cell cycle stage-specific probes are used, as mentioned above.

To assess the effect on transgene integration, growth of bialaphos-resistant colonies on selective medium is a reliable assay. Within 1–7 days after DNA introduction, the embryos are moved onto culture medium containing 3 mg/l of the selective agent bialaphos. Embryos, and later callus, are transferred to fresh selection plates every 2 weeks. After 6–8 weeks, transformed calli are recovered. Transgenic callus containing the introduced genes can be verified using PCR and Southern analysis. Northern analysis can also be used to verify which calli are expressing the bar gene, and/or the prohibitin-antisense construct. In immature embryos that had transient, elevated prohibitin-antisense expression, higher numbers of stable transformants are recovered (likely a direct result of increased integration frequencies). Increased trangene integration frequency can also be assessed using such well-established labeling methods such as in situ hybridization.

For this specific application (using transient prohibitin-antisense-mediated cell cycle stimulation to increase transient integration frequencies), it may be desirable to reduce the likelihood of ectopic stable expression of prohibitin-antisense. Strategies for transient-only expression can be used. This includes delivery of RNA (transcribed from the prohibitin-antisense construct) along with the transgene cassettes to be integrated to enhance transgene integration by transient stimulation of cell division. Using well-established methods to produce prohibitin-antisense-RNA, this can then be purified and introduced into maize cells using physical methods such as microinjection, bombardment, electroporation or silica fiber methods.

Example 4

Use of Antisense Oligonucleotides Against Prohibitin to Transiently Stimulate Cell Division and Enhances Transgene Integration An alternative to conventional antisense strategies is the use of antisense oligonucleotides (often with chemically-modified nucleotides). Such an antisense oligonucleotide, typically a 15–18 mer (but this size can vary either more or less), is designed to bind around accessible regions such as the ribosomal binding site around the "Start" codon. Introduction of the antisense oligonucleotide into a cell will transiently stop expression of the targeted gene. For example, an antisense oligonucleotide of between 15 to 18 nucleotides in length, that is complementary (in reverse orientation) to the sequence surrounding the Start codon of the prohibitin structural gene, is introduced into maize cells. These methods of introduction for the oligonucleotide are similar to those previously described above for introduction of plasmids. In cells that receive such an antisense oligonucleotide targeted to prohibitin, the antisense oligonucleotide transiently disrupts prohibitin expression and stimulates entry into S-phase (as observed in mammalian cells—see Nuell et al., (1991) *Mol. Cell. Biology* 11(3) :1372–1381).

Example 5

Use of Antibodies Raised Against Prohibitin to Transiently Stimulate Cell Division and Enhances Transgene Integration Antibodies directed against prohibitin can also be used to mitigate prohibitin's tumor suppressor activity, thus stimulating the cell cycle and transgene integration. Genes encoding single chain antibodies, expressed behind a suitable promoter, for example the ubiquitin promoter, could be used in such a fashion. Transient expression of an anti-prohibitin antibody could temporarily disrupt normal prohibitin tumor suppressor function and thus stimulate the cell cycle. Alternatively, antibodies raised against prohibitin could be purified and used for direct introduction into maize cells. The antibody is introduced into maize cells using physical methods such as microinjection, bombardment, electroporation or silica fiber methods. Alternatively, single chain anti-prohibitin is delivered from *Agrobacterium tumefaciens* into plant cells in the form of fusions to Agrobacterium virulence proteins. Fusions are constructed between the anti-prohibitin single chain antibody and bacterial virulence proteins such as VirE2, VirD2, or VirF which are known to be delivered directly into plant cells. Fusions are constructed to retain both those properties of bacterial virulence proteins required to mediate delivery into plant cells and the anti-prohibitin activity required for stimulating cell division and enhancing transgene integration. This method ensures a high frequency of simultaneous co-delivery of T-DNA and functional anti-prohibitin protein into the same host cell.

The methods above represent various means of using the prohibitin-antisense or anti-prohibitin antibodies, or antisense oligonucleotides to transiently stimulate DNA replication and cell division, which in turn enhances transgene integration by providing an improved cellular/molecular environment for this event to occur.

Example 6

Altering Prohibitin Expression Stimulates the Cell Cycle and Growth

Based on results in other eukaryotes, expression of the ZmProhibitin gene should block the G1/S transition and prevent cell division. This decrease in division rate is assessed in a number of different manners, being reflected in larger cell size, less rapid incorporation of radiolabeled nucleotides, and slower growth (i.e. less biomass accumulation). Conversely, expression of prohibitin antisense (or an appropriate antisense oligonucleotide, or anti-prohibitin antibody) will result in smaller cells, more rapid incorporation of radiolabeled nucleotides, and faster growth. Delivery of the prohibitin-antisense in an appropriate plant expression cassette is accomplished through numerous well-established methods for plant cells, including for example particle bombardment, sonication, PEG treatment or electroporation of protoplasts, electroporation of intact tissue, silica-fiber methods, microinjection or Agrobacterium-mediated transformation. As an alternative to conventional deliver of bacterial plasmids, introduction of a viral plasmid from which a prohibitin-antisense sequence is expressed could also be employed. The result of ZmProhibitin-antisense expression will be to stimulate the G1/S transition and hence cell division, providing the optimal cellular environment for integration of introduced genes. This will trigger a tissue culture response (cell divisions) in genotypes that typically do not respond to conventional culture techniques, or stimulate growth of transgenic tissue beyond the normal rates observed in wild-type (non-transgenic) tissues. To demonstrate this, the prohibitin-antisense gene is cloned into a cassette with a constitutive promoter (i.e. either a strong maize promoter such as the ubiquitin promoter including the first ubiquitin intron, or a weak constitutive promoter such as nos). Either particle-mediated DNA delivery or Agrobacterium-mediated delivery are used to introduce the UBI::ZmProhibitin::pinII-containing plasmid along with a UBI::bar::pinII-containing plasmid into maize cells capable of growth on suitable maize culture medium. Such competent cells can be from maize suspension culture, callus culture on solid medium, freshly isolated immature embryos or meristem cells. Immature embryos of the Hi-II genotype are used as the target for co-delivery of these two plasmids, and within 1–7 days the embryos are moved onto culture medium containing 3 mg/l of the selective agent bialaphos. Embryos, and later callus, are transferred to fresh selection plates every 2 weeks. After 6–8 weeks, transformed calli are recovered. In treatments where both the bar gene and prohibitin-antisense gene have been transformed into immature embryos, a higher number of growing calli are recovered on the selective medium and callus growth is stimulated (relative to treatments with the bar gene alone). When the prohibitin-antisense gene is introduced without any additional selective marker, transgenic calli can be identified by their ability to grow more rapidly than surrounding wild-type (non-transformed) tissues. Transgenic callus can be verified using PCR and Southern analysis. Northern analysis can also be used to verify which calli are expressing the bar gene, and which are expressing the maize Prohibitin gene at levels above normal wild-type cells (based on hybridization of probes to freshly isolated mRNA population from the cells).

Inducible Expression:

The prohibitin-antisense gene can also be cloned into a cassette with an inducible promoter such as the benzenesulfonamide-inducible promoter. The expression vector is co-introduced into plant cells and after selection on bialaphos, the transformed cells are exposed to the safener (inducer). This chemical induction of prohibitin-antisense expression results in stimulated G1/S transition and more rapid cell division. The cells are screened for the presence of Zmprohibitin-antisense RNA by northern, or RT-PCR (using transgene specific probes/oligo pairs). Increased DNA replication is detected using BrdU labeling followed by antibody detection of cells that incorporated this thymidine analogue. Likewise, other cell cycle division assays could be employed, as described above.

Example 7

Control of Prohibitin-antisense Expression Using Tissue-preferred or Cell-specific Promoters Provides a Differential Growth Advantage Prohibitin-antisense expression using tissue-preferred or cell-specific promoters stimulates cell cycle progression in the expressing tissues or cells. For example, using a seed-specific promoter will stimulate cell division rate and result in increased seed biomass. Alternatively, driving prohibitin-antisense expression with a strongly-expressed, early, tassel-specific promoter will enhance development of this entire reproductive structure. Expression of prohibitin antisense in other cell types and/or at different stages of development will similarly stimulate cell division rates.

Example 8

Meristem Transformation

Meristem transformation protocols rely on the transformation of apical initials or cells that can become apical initials following reorganization due to injury or selective pressure. The progenitors of these apical initials differentiate to form the tissues and organs of the mature plant (i.e. leaves, stems, ears, tassels, etc.). The meristems of most angiosperms are layered with each layer having its own set of initials. Normally in the shoot apex these layers rarely mix. In maize the outer layer of the apical meristem, the L1, differentiates to form the epidermis while descendents of cells in the inner layer, the L2, give rise to internal plant parts including the gametes. The initials in each of these layers are defined solely by position and can be replaced by adjacent cells if they are killed or compromised. Meristem transformation frequently targets a subset of the population of apical initials and the resulting plants are chimeric. If for example, 1 of 4 initials in the L1 layer of the meristem are transformed only ¼ of epidermis would be transformed. Selective pressure can be used to enlarge sectors but this selection must be non-lethal since large groups of cells are required for meristem function and survival. Transformation of an apical initial with a prohibitin-antisense sequence under the expression of a promoter active in the apical meristem (either meristem-specific or constitutive) would allow the transformed cells to grow faster and displace wild-type initials driving the meristem towards homogeneity and minimizing the chimeric nature of the plant body. To demonstrate this, the prohibitin-antisense sequence is cloned into a cassette with a promoter that is active within the meristem (i.e. either a strong constitutive maize promoter such as the ubiquitin promoter including the first ubiquitin intron, or a promoter active in meristematic cells such as the maize histone, cdc2 or actin promoter). Coleoptilar stage embryos are isolated and plated meristem up on a high sucrose maturation medium (see Lowe et al., 1997, In *Genetic Biotechnology and Breeding of Maize and Sorghum*, A S Tsaftaris, ed., Royal Society of chemistry, Cambridge, UK, pp94–97). The prohibitin-antisense expression cassette along with a reporter construct such as Ubi:GUS:pinII can then be co-delivered (preferably 24 hours after isolation) into the exposed apical dome using conventional particle gun transformation protocols. As a control the prohibitin-antisense construct can be replaced with an equivalent amount of pUC plasmid DNA. After a week to 10 days of culture on maturation medium the embryos can be transferred to a low sucrose hormone-free germination medium. Leaves from developing plants can be sacrificed for GUS staining. Transient expression of the prohibitin-antisense sequence in meristem cells, through stimulation of the G1_S transition, will result in greater integration frequencies and hence more numerous transgenic sectors. Integration and expression of the prohibitin-antisense sequence will impart a competitive advantage to expressing cells resulting in a progressive enlargement of the transgenic sector. Due to the enhanced growth rate in prohibitin-antisense-expressing meristem cells, they will supplant wild-type meristem cells as the plant continues to grow. The result will be both enlargement of transgenic sectors within a given cell layer (i.e. periclinal expansion) and into adjacent cell layers (i.e. anticlinal invasions). As cells expressing the prohibitin-antisense occupy an increasingly large proportion of the meristem, the frequency of transgene germline inheritance goes up accordingly.

Example 9

Use of Flp/Frt System to Excise the Prohibitin-antisense Cassette

In cases where the prohibitin-antisense has been integrated and prohibitin-antisense expression is useful in the recovery of maize transgenics, but is ultimately not desired in the final product, the prohibitin-antisense expression cassette (or any portion thereof that is flanked by appropriate FRT recombination sequences) can be excised using FLP-mediated recombination.

Example 10

Expressing the prohibitin gene under the control of a cell-specific or tissue-preferred or a developmentally-regulated promoter will result in the cessation of growth in these cells or tissues. For example, using a tapetum-specific promoter or a microspore-specific promoter, expression of prohibitin will result in aborted pollen development and male sterility. For certain uses such as hybrid production it may also be desirable to completely eliminate the male or female inflorescence. Expressing prohibitin at early stages of ear or tassel development will result in failure of these organs to develop.

Example 11

Identification of a Novel Protein Superfamily that Controls Cell Proliferation, Ion Channel Regulation, and Cell Death A novel protein superfamily named PID, for Proliferation, Ion and Death, was identified. The new superfamily is comprised of three protein families, each respectively containing members involved in cell proliferation, ion conductance, and cell death. The members of the superfamily include many animal, bacteria, plant and fungi sequences representing prohibiting, NG1-like proteins (referred to as HIR proteins for Hypersensitive Induced Reaction), stomatins, and other membrane proteins. The structures of the superfamily members were analyzed with the goal of understanding their functional roles and molecular mechanisms that may explain and reconcile their involvement in apparently diverse physiological processes.

Methods:

The HIR, prohibitin and stomatin homologues were identified with the aid of the IRIS software package from HGS, which includes the Blast algorithm. The alignment program indicated homology between tobacco NG1 (Genbank accession U66271) and to prohibitins from various species, and to human stomatin (Genbank accession U33925). Full-insert sequences were produced at Pioneer by forward and reverse sequencing and primer walking using an A.B.I. 377 sequencing machine. Sequences were assembled using Sequencher™ version 3.0 (Gene Codes Corporation, Ann Arbor, Mich.) and/or AssemblyLIGN™ (Eastman Kodak Company, New Haven, Conn.) software.

Initial database searches were carried out by BLASTP program (Altschul et al. (1990) *J. Mol. Biol.* 215:403–410) with chickpea HIR-like gene as a probe followed by PSI-BLAST (Altschul et al., (1997) *Nucleic Acids Res.* 25:33 89–3402) with default parameters (Blosum 62, Gap existence cost 11, Per residue gap cost 1, Lambda ratio 0.85, Expect Threshold 10). About 32 sequences that appeared as significant hits, both in terms of statistical threshold and the type, were multiply aligned by ClustalW program with default parameters (Thompson et al., (1994) *Nucleic Acids Res.* 22:4673–4680).

Highly conserved residues were identified to generate a profile to perform further database searches by PHI-BLAST program (Zhang et al., (1998) *Nucleic Acids Res.* 26:3086–3990). Phylogenetic analysis was carried out by using the option within CLUSTALW (Higgins et al., (1996) *Methods Enzymol* 266:383–402) to generate multiple alignments followed by distance calculations and tree constructions with the PROTDIST and Neighbor-joining program of the PHYLIP package main.html—Felsenstein (Felsenstein (1993) PHYLIP (Phylogeny Inference Package) version 3.5c. Department of Genetics, University of Washington, Seattle). Pair-wise alignments were performed by GAP program within the GCG package (Felsenstein (1994) PHYLIP (Phylogeny Inference Package) version 8. Department of Genetics, University of Washington, Seattle).

After sufficient grounds were established for a possible evolutionary relationships among the sequences, further structural analyses were carried out notably by hydropathy profiles using Kyte-Doolittle method with a 19 residue sliding window (http://bioinformatics.weizmann.ac.il/hydroph/cmp_hydph.html). Secondary structure predictions were carried out by DSC algorithm (King et al. (1997) *CABIOS* 13:473–474). In order to look for conserved motifs in the 32 members included in the multiple alignment, we applied MEME algorithm which resulted in the detection of four highly conserved motifs (Grundy et al. (1997) *Biochem. Biophys. Res. Commun.* 231:760–766.

Results:

Three distinct full-length maize cDNAs named Zm-HIR1, Zm-HIR2, and Zm-HIR3, for Zea mays Hypersensitive Induced Reaction genes one, two and three, respectively have been identified (U.S. patent application Ser. No. 09/256,158 filed on Feb. 24, 1999 entitled "Genes for Activation of Plant Defense Systems") and share high homology to the tobacco NG1 peptide (Genbank accession U66271). Initial searches of maize HIR genes against the public database using the BLAST program (Altschul et al. (1990) *J. Mol. Biol.* 215:403–410) indicated some similarity to prohibitins and stomatins. For maize stomatin sequences see U.S. Provisional Application entitled "Plant Stomatin Genes and Their Use" filed concurrently herewith.

The coding region lengths for the HIR proteins (242–286 aa) are comparable to those of prohibitins (272–289 aa), and of stomatins and other membrane-associated proteins (249–481 aa). Pair-wise amino acid similarities of plant HIR and HIR-like genes with maize prohibitins were between 28–36% similar, and with maize stomatin between 34–37% similar. This suggested that the maize HIR genes were somewhat closer in amino acid sequence to stomatins than to prohibiting.

The non-redundant protein database at NCBI was searched using the PSI-BLAST program (Altschul et al. (1997) *Nucleic Acids Res.* 25:3389–3402) with a hypothetical protein from Chickpea (accession gi|3928150) as a probe, which has over 90% amino acid similarity with the maize HIR proteins. This search identified many genes, including stomatins and integral membrane proteins (E=<$10^{-6}$) and prohibitins (E=<$10^{-8}$), and HFLK/HFLC proteins (E=<$10^{-6}$). These sequences were used to generate an unrooted dendogram which revealed a large superfamily with at least four constituent families. The stomatins and integral membrane proteins formed a large family that may possibly have some ion channel regulating activity in different organisms. A second family was composed of HIR and HIR-like sequences. The stomatin/integral membrane family was most closely related to this HIR family. The third family was composed of prohibitins and related sequences. The bacterial membrane proteins HFLK/BFLC formed a small fourth family more closely related to the prohibitin-containing family.

A Comparison of hydropathy plots of maize HIR sequence with prohibitins from maize and *Trypanosoma brucei* revealed similar structural profiles. A similar comparison of a stomatin-like gene from Synchocystis sp. with Trypanosoma prohibitin also indicated structural similarity between several regions of these genes. The shared hydropathy plots indicate there are conserved structural features between these diverse proteins from widely diverged phyla, and thus suggests that the members at some level may possess a conserved function.

Amino acid sequences for 32 members of this superfamily were aligned to reveal shared and diverged features. Several regions are highly conserved and aligned well with fewer gaps. Two residues, an Aspartate and an Alanine, are completely conserved among all the proteins, and are located in the conserved secondary structural elements suggesting a critical role for these residues in the biological function of these proteins. The conserved Aspartate residue in the prohibitin sequences of the invention is at amino acid position 94, 89, 90, and 94 for SEQ ID NOS: 2, 4, 6 and 8, respectfully. The conserved Alanine residue is at amino acid position 199, 194, 195, and 199 for SEQ ID NOS: 2, 4, 6 and 8, respectfully.

A systematic search for conserved motifs in the 32 members of the superfamily was performed using the MEME algorithm. The MEME motifs have been indicated as reliable indicators of family membership (Grundy et al. (1997) *Biochem. Biophys. Res. Commun.* 231:760–766). The search resulted in the identification of four conserved motifs with a very high E-values. All four motifs are present in all members of HIR, somatin and prohibition families. Additionally, the localization of these four motifs in all these genes appears to be spatially well conserved, indicating the possibility for a similar structural orientation in three-dimensional space. We are unaware of any reports that members of this superfamily have been structurally resolved.

The HFLK/HFLC proteins contain only Motif 3. Hydropathy analysis also indicated that these genes have fewer structural similarities in common with other members in this superfamily. The HFLK/HFLC are bacterial membrane proteins with protease activity, and are involved in lysogenization. They appear to be more distantly related from the other members of this superfamily.

Based upon the alignment and the motifs derived from MEME algorithm, we created a PROSITE regular expression from a conserved region and used it to search the protein database as a pattern seed by PHI-BLAST program (Zhang et al. (1998) *Nucleic Acids Res.* 26:3986–3990). This algorithm has been reported to be very useful for identify genes that share a pattern that is indicative of functional relationship. By this approach we retrieved 98 sequences that contained the pattern—[ILM]-[RK]-X(2)-[VLI]-[PGA]-X(10, 11 )-[RX]-X(2)-[IVLI]-X(7)-[IVLIM]-X(6)-[WFY]- which were above the threshold of 0.001 and displayed very significant E-values. Of these the HIR proteins, stomatins and other membrane-associated proteins had E values <$10^{-4}$, and prohibitins had relatively higher E values (E=0.003–10.0). Considering the size of the database searched and the functionally divergent sequences in this superfamily, the seed pattern used has been shown by this search method to be highly effective at successfully retrieving members for each of the three families of this superfamily. Consequently, this pattern possibly represents a signature for this newly identified PID superfamily. This signature sequence is found in prohibitin sequences of the present invention between amino acid resides 137–171 of SEQ ID NO:2, amino acid residues 132–166 of SEQ ID NO:4, amino acid residues of 133–167 of SEQ ID NO:6, and amino acid residues 137–171 of SEQ ID NO:8.

In the PROSITE dictionary, stomatin (Band 7) signature is in part present in HIR proteins, having diverged by about 40% (at seven out of sixteen positions in the stomatin signature, when conservative substitutions are considered. The PID superfamily signature we identified partially overlaps the PROSITE Band 7 signature, however the PID signature predicts all superfamily members and not just the stomatins. The PID signature actually overlaps with Motif 1 region as discovered by MEME algorithm. Although Motif 1 is not well conserved in HFLK/HFLC proteins, the PID signature is conserved in HFLK/HFLC, indicating that these proteins are distant members of this superfamily.

The sequence and structural similarities of plant HIR proteins with prohibiting, stomatins and other integral membrane proteins, some of which, in particular stomatins, regulate ion channel function, suggests that the HIR proteins are involved in hypersensitive reaction and cell death through the regulation of ion channel activity. The C-terminal region of stomatin is very rich in alpha-helical content and has been postulated to act as a plug to regulate potassium ion channels (Stewart et al. (1993) *Biochimica et Biophysica Acta.* 1225:15–25; Stewart (1997) *Int. J. Biochem. Cell Biol.* 29:271–274). The HIR proteins also have C-termini with very high in helical content, suggesting a similar structure and function of this region to that of the stomatin C-termini.

In conclusion, a supergene family named PID (Proliferation, Ion, and Death) has been identified. Members of the family include prohibitins and stomatins and the HIR genes. Proteins of this superfamily are involved in diverse functions, but their structural similarity suggests a conserved molecular mechanism.

| 272 V | | |
|---|---|---|
| Ingredient | Amount | Unit |
| D-I H$_2$O | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:

@=Add after bringing up to volume

Dissolve ingredients in polished D-I H$_2$O in sequence

Adjust to pH 5.6

Bring up to volume with polished D-I H$_2$O after adjusting pH

Sterilize and cool to 60° C.

=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.

Total Volume (L)=1.00

| 288 J | | |
|---|---|---|
| Ingredient | Amount | Unit |
| D-I H$_2$O | 950.000 | Ml |
| MS Salts | 4.300 | G |

-continued

| 288 J | | |
|---|---|---|
| Ingredient | Amount | Unit |
| Myo-Inositol | 0.100 | G |
| MS Vitamins Stock Solution ## | 5.000 | Ml |
| Zeatin 5 mg/ml | 1.000 | Ml |
| Sucrose | 60.000 | G |
| Gelrite # | 3.000 | G |
| Indoleacetic Acid 0.5 mg/ml # | 2.000 | Ml |
| 0.1 mM Abscisic Acid | 1.000 | Ml |
| Bialaphos 1 mg/ml # | 3.000 | Ml |

Directions:

@=Add after bringing up to volume

Dissolve ingredients in polished D-I $H_2O$ in sequence

Adjust to pH 5.6

Bring up to volume with polished D-I $H_2O$ after adjusting pH

Sterilize and cool to 60° C.

Add 3.5 g/L of Gelrite for cell biology.

=Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L)=1.00

| 560 R | | |
|---|---|---|
| Ingredient | Amount | Unit |
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine.HCL 0.4 mg/ml | 1.250 | Ml |
| Sucrose | 30.000 | G |
| 2, 4-D 0.5 mg/ml | 4.000 | Ml |
| Gelrite @ | 3.000 | G |
| Silver Nitrate 2 mg/ml # | 0.425 | Ml |
| Bialaphos 1 mg/ml # | 3.000 | Ml |

Directions:

@=Add after bringing up to volume

=Add after sterilizing and cooling to temp.

Dissolve ingredients in D-I $H_2O$ in sequence

Adjust to pH 5.8 with KOH

Bring up to volume with D-I $H_2O$

Sterilize and cool to room temp.

Total Volume (L)=1.00

| 560 Y | | |
|---|---|---|
| Ingredient | Amount | Unit |
| D-I Water, Filtered | 950.000 | Ml |
| CHU (N6) Basal Salts (SIGMA C-1416) | 4.000 | G |
| Eriksson's Vitamin Mix (1000X SIGMA-1511) | 1.000 | Ml |
| Thiamine.HCL 0.4 mg/ml | 1.250 | Ml |
| Sucrose | 120.000 | G |
| 2,4-D 0.5 mg/ml | 2.000 | Ml |
| L-Proline | 2.880 | G |
| Gelrite @ | 2.000 | G |
| Silver Nitrate 2 mg/ml # | 4.250 | Ml |

Directions:

@=Add after bringing up to volume

=Add after sterilizing and cooling to temp.

Dissolve ingredients in D-I $H_2O$ in sequence

Adjust to pH 5.8 with KOH

Bring up to volume with D-I $H_2O$

Sterilize and cool to room temp.

Autoclave less time because of increased sucrose

Total Volume (L)=1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence set forth in SEQ ID NO: 1.

2. An isolated nucleic acid molecule comprising a nucleotide sequence set forth in SEQ ID NO: 3.

3. An isolated nucleic acid molecule comprising a nucleotide sequence set forth in SEQ NO: 5.

4. An isolated nucleic acid molecule comprising a nucleotide sequence set forth in SEQ ID NO: 7.

5. An isolated nucleic acid molecule comprising a nucleotide sequence selected from the group consisting of:
   a) a nucleotide sequence comprising a cDNA sequence deposited as Patent Deposit Nos. 98867, 98868, 98869, or 98870;
   b) a nucleotide sequence encoding a polypeptide comprising an amino acid sequence set forth in SEQ ID NO: 2, 4, 6, or 8; and,
   c) a nucleotide sequence comprising an antisense sequence fully complementary to the sequence set forth in SEQ ID NO: 1, 3, 5, or 7.

6. An expression cassette comprising a nucleotide sequence of claim 5, wherein said nucleotide sequence is operably linked to a promoter.

7. The expression cassette of claim 6, wherein said promoter is a constitutive promoter.

8. A vector comprising the expression cassette of claim 6.

9. A plant having stably incorporated into its genome a nucleotide sequence operably linked to a heterologous promoter active in said plant, said nucleotide sequence selected from the group consisting of:
   a) a nucleotide sequence set forth in SEQ ID NO: 1, 3, 5, or 7;

b) a nucleotide sequence comprising a cDNA sequence deposited as Patent Deposit Nos. 98867, 98868, 98869, or 98870; and, c) a nucleotide sequence encoding a polypeptide comprising an amino acid sequenc[0085] set forth in SEQ ID NO: 2, 4, 6 or 8.

10. The plant of claim 9, wherein said plant is a monocot.

11. The plant of claim 10, wherein said monocot is maize.

12. The plant of claim 9, wherein said plant is a dicot.

13. A transformed seed of the plant of claim 9.

14. A transformed seed of the plant of claim 10.

15. An plant cell having stably incorporated into its genome a nucleotide sequence operably linked to a heterologous promoter active in said plant cell, said nucleotide sequence selected from the group consisting of:

a) a nucleotide sequence set forth in SEQ ID NO: 1, 3, 5, or 7;

b) a nucleotide sequence comprising a cDNA sequence deposited as Patent Deposit Nos. 98867, 98868, 98869, or 98870; and, c) a nucleotide sequence encoding a polypeptide comprising an amino acid sequence set forth in SEQ ID NO: 2, 4, 6, or 8.

16. The plant cell of claim 15, wherein said plant cell is from a monocot.

17. The plant cell of claim 16, wherein said monocot is maize.

18. The plant cell of claim 15, wherein said plant cell is from a dicot.

19. A method of modulating the level of a prohibitin polypeptide in a plant comprising stably incorporating into the genome of said plant a nucleotide sequence operably linked to a heterologous promoter active in said plant, said nucleotide sequence selected from the group consisting of:

a) a nucleotide sequence set forth in SEQ ID NO: 1, 3, 5, or 7;

b) a nucleotide sequence comprising a cDNA sequence deposited as Patent Deposit Nos. 98867, 98868, 98869, or 98870;

c) a nucleotide sequence encoding a polypeptide comprising the amino acid sequence set forth in SEQ ID NO: 2, 4, 6 or 8 and d) a nucleotide sequence comprising an antisense sequence fully complementary to the sequence set forth in SEQ ID NO: 1, 3, 5, or 7.

20. The method of claim 19, wherein said plant is a monocot.

21. The method of claim 20, wherein said monocot is maize.

22. The method of claim 19, wherein said promoter is a constitutive promoter.

23. The method of claim 22, wherein said constitutive promoter is selected from the group consisting of a core promoter of a Rsyn7 promoter and a core promoter of a 35S promoter.

24. The method of claim 19, wherein said promoter is an inducible promoter.

* * * * *

UNITED STATES PATENT AND TRADEMARK OFFICE
CERTIFICATE OF CORRECTION

PATENT NO. : 6,441,151 B1  Page 1 of 1
DATED : August 27, 2002
INVENTOR(S) : Gordon-Kamm et al.

It is certified that error appears in the above-identified patent and that said Letters Patent is hereby corrected as shown below:

<u>Title page, Item [54] and Column 1, line 1,</u>
Title, "PROHIBITION" should read -- PROHIBITIN --.

Item [56], References Cited, OTHER PUBLICATIONS, "Sato et al., reference", "Prohibition" should read -- Prohibitin --.

<u>Column 35,</u>
Table, line 8, "Zeatin 5 mg/ml" should read -- Zeatin .5 mg/ml --;
Line 10, "Gelrite #" should read -- Gelrite @ --.

<u>Columm 49,</u>
Line 5, "sequenc[0085]" should read -- sequence --.

<u>Column 50,</u>
Line 13, after "8" insert -- ; --.

Signed and Sealed this

Twenty-fifth Day of February, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 1323
<212> TYPE: DNA
<213> ORGANISM: Zea mays
<220> FEATURE:
<221> NAME/KEY: misc_feature
<222> LOCATION: (0)...(0)
<223> OTHER INFORMATION: Prohibitin - ZmPHB1

<400> SEQUENCE: 1

-continued

```
ctttatccgc acctccgtat ccacgcctcg cacttcataa gattcggagc caacagtgct      60
ggagttggtc tgagcatccc tatttgtagg acgctccccc tctagtcatc tcctcaaaca     120
aaaaccctag ccgccgcgcc gccccgctcc ctagtggtcc tccctccccc accactgcag     180
ctccgtcccg gcggcccaa gagttgcgg gaggatgaac gtgaagggcg gcagccggat       240
tccggtaccc cctccggggg ccagcgcgct ggtcaaggtg gccgtgttcg gcggcgccgc     300
cgtgtacgct gccgtgaaca gcctctacaa cgtcgagggt gggcaccgcg ccatcgtctt     360
caaccgcatc caggggatca aggacaaggt ataccccgaa gggactcact ttatgattcc     420
atggtttgaa cgaccaatca tttatgatgt ccgtgctcga ccgaatcttg ttgagagtac     480
ttctgggagt cgggatcttc agatggtgaa aattggtctc cgtgtcctta caaggcctat     540
gccagagagg ctaccacata tctacagaac tctgggagag aacttcaatg agagagtttt     600
gccttcaatc atccatgaaa cactgaaagc tgttgttgct caatataatg ctagtcagct     660
gatcacacag agagagactg tgagtaggga gattaggaag atactgactg agagggctag     720
attcttcaac attgctcttg atgacgtctc catcacaagc ctgagctttg ggaaggagtt     780
tactcatgcc attgaagcga agcaggttgc tgcacaggaa gctgagcgtg ctaagttcat     840
tgtcgagaaa gctgaacaag ataagagaag tgcaattatc agggctcagg agaggctaa      900
gagtgcggag ctgattggtc aagccatagc gaacaaccct gccttccttg ccctgaggca     960
gattgaagct gcaagggaga ctctcccacac catttcggcc tcagccaaca aggtgttcct    1020
ggactccaac gacctgctgc tcaacctcca gcagctgaat gtatcgagca agcagaagaa    1080
atgatgtcac aacgttatcc cctttcttct gagtttgcag tcagtagtgg atgcctttgt    1140
accagacatt gtgaggaacg ctcggttttg gatgtagttt cgccaatctt cctgttatgt    1200
ggaacttgcg agtatttgct caaaggcaag caagctgaca ggttttgttt aaacgtaact    1260
acaggatgag aaagttttca ataaggaaca aattctgtta tgccaccaaa aaaaaaaaa    1320
aaa                                                                  1323
```

```
<210> SEQ ID NO 2
<211> LENGTH: 289
<212> TYPE: PRT
<213> ORGANISM: Zea mays

<400> SEQUENCE: 2

Met Asn Val Lys Gly Gly Ser Arg Ile Pro Val Pro Pro Gly Ala
  1               5                  10                  15

Ser Ala Leu Val Lys Val Ala Val Phe Gly Gly Ala Ala Val Tyr Ala
                 20                  25                  30

Ala Val Asn Ser Leu Tyr Asn Val Glu Gly Gly His Arg Ala Ile Val
             35                  40                  45

Phe Asn Arg Ile Gln Gly Ile Lys Asp Lys Val Tyr Pro Glu Gly Thr
         50                  55                  60

His Phe Met Ile Pro Trp Phe Glu Arg Pro Ile Ile Tyr Asp Val Arg
 65                  70                  75                  80

Ala Arg Pro Asn Leu Val Glu Ser Thr Ser Gly Ser Arg Asp Leu Gln
                 85                  90                  95

Met Val Lys Ile Gly Leu Arg Val Leu Thr Arg Pro Met Pro Glu Arg
            100                 105                 110

Leu Pro His Ile Tyr Arg Thr Leu Gly Glu Asn Phe Asn Glu Arg Val
            115                 120                 125
```

-continued

```
Leu Pro Ser Ile Ile His Glu Thr Leu Lys Ala Val Val Ala Gln Tyr
    130                 135                 140
Asn Ala Ser Gln Leu Ile Thr Gln Arg Glu Thr Val Ser Arg Glu Ile
145                 150                 155                 160
Arg Lys Ile Leu Thr Glu Arg Ala Arg Phe Phe Asn Ile Ala Leu Asp
                165                 170                 175
Asp Val Ser Ile Thr Ser Leu Ser Phe Gly Lys Glu Phe Thr His Ala
                180                 185                 190
Ile Glu Ala Lys Gln Val Ala Ala Gln Glu Ala Glu Arg Ala Lys Phe
            195                 200                 205
Ile Val Glu Lys Ala Glu Gln Asp Lys Arg Ser Ala Ile Ile Arg Ala
    210                 215                 220
Gln Gly Glu Ala Lys Ser Ala Glu Leu Ile Gly Gln Ala Ile Ala Asn
225                 230                 235                 240
Asn Pro Ala Phe Leu Ala Leu Arg Gln Ile Glu Ala Ala Arg Glu Ile
                245                 250                 255
Ser His Thr Ile Ser Ala Ser Ala Asn Lys Val Phe Leu Asp Ser Asn
                260                 265                 270
Asp Leu Leu Leu Asn Leu Gln Gln Leu Asn Val Ser Ser Lys Gln Lys
            275                 280                 285
Lys
```

<210> SEQ ID NO 3
<211> LENGTH: 1162
<212> TYPE: DNA
<213> ORGANISM: Zea mays
<220> FEATURE:
<221> NAME/KEY: misc_feature
<222> LOCATION: (0)...(0)
<223> OTHER INFORMATION: Prohibitin - ZmPHB2

<400> SEQUENCE: 3

```
aacccctgca aaacccgcc  actctcagat ccgcacagcg acgccgccag ccagacccga     60
tccctccct  cgctagggtt ttcgtccccg cgccgccgcg ctcccggatc caccgaaac    120
aaccatggcc ggcggtcccg cggcggtgtc gttcctgacc aacatcgcga aggtggctgc    180
ggggctcgga gccgcggcct cgctcgcctc cgcgtcgctc tacaccgtcg acggcggcga    240
gcgcgccgtc atcttcgacc gtttccgcgg ggtgctcccg gagaccgtcg gcgagggcac    300
ccatttcctc gtgccctggc tgcagaagcc cttcatcttc gacatccgca cgcgcccgca    360
caacttctcc tccaactcgg ggaccaagga cctgcagatg gtcaacctca cgctccgtct    420
cctctcccgc cccgacgtcc agcacctccc caccatcttc acctccctcg gactcgagta    480
cgacgacaaa gtgctcccct ccatcggcaa cgaggtgctc aaggccgtcg tcgcccagtt    540
caatgccgac cagctcctca ccgaccgccc ccacgtctcc gccctcgtcc gcgacgctct    600
catccgccgc gcccgcgagt tcaacatcat cctcgacgac gtcgccatca cccacctctc    660
ctatggtatc gagttctcgc tggccgttga agaagcag gtcgcgcagc aggaggccga    720
gcgctccaag ttcctcgtcg ccaaggcgga gcaggagagg cggcggcca tcgtgcgcgc    780
tgagggagag agcgagtccg cgcgcctcat ctctgaggcc acggcgatgg ctgggacagg    840
gctgatcgag ctcaggagga tcgaggcggc caaggagatt gccgcagagc tggctcgctc    900
accgaatgtg gcatacattc cttctgggga aaacggaaag atgctgcttg gtctcaatgc    960
tactggattt ggccggtgat tcactgtttt tttagtctgc ttgtgctatg tgctgatgca   1020
tgactaaaac ggaggttcga actttgaagg acagtgatat ctgctatcct tgcttatgtt   1080
```

```
aagttttcct tgtcttggaa ctaaatgtgt ctgttgtgct ccaaataagt tttggttttt   1140
gactgcaaaa aaaaaaaaaa aa                                           1162
```

<210> SEQ ID NO 4
<211> LENGTH: 284
<212> TYPE: PRT
<213> ORGANISM: Zea mays

<400> SEQUENCE: 4

```
Met Ala Gly Gly Pro Ala Ala Val Ser Phe Leu Thr Asn Ile Ala Lys
  1               5                  10                  15

Val Ala Ala Gly Leu Gly Ala Ala Ser Leu Ala Ser Ala Ser Leu
                 20                  25                  30

Tyr Thr Val Asp Gly Gly Glu Arg Ala Val Ile Phe Asp Arg Phe Arg
                 35                  40                  45

Gly Val Leu Pro Glu Thr Val Gly Glu Gly Thr His Phe Leu Val Pro
     50                  55                  60

Trp Leu Gln Lys Pro Phe Ile Phe Asp Ile Arg Thr Arg Pro His Asn
 65                  70                  75                  80

Phe Ser Ser Asn Ser Gly Thr Lys Asp Leu Gln Met Val Asn Leu Thr
                 85                  90                  95

Leu Arg Leu Leu Ser Arg Pro Asp Val Gln His Leu Pro Thr Ile Phe
                100                 105                 110

Thr Ser Leu Gly Leu Glu Tyr Asp Asp Lys Val Leu Pro Ser Ile Gly
                115                 120                 125

Asn Glu Val Leu Lys Ala Val Val Ala Gln Phe Asn Ala Asp Gln Leu
    130                 135                 140

Leu Thr Asp Arg Pro His Val Ser Ala Leu Val Arg Asp Ala Leu Ile
145                 150                 155                 160

Arg Arg Ala Arg Glu Phe Asn Ile Ile Leu Asp Asp Val Ala Ile Thr
                165                 170                 175

His Leu Ser Tyr Gly Ile Glu Phe Ser Leu Ala Val Glu Lys Lys Gln
                180                 185                 190

Val Ala Gln Gln Glu Ala Glu Arg Ser Lys Phe Leu Val Ala Lys Ala
                195                 200                 205

Glu Gln Glu Arg Arg Ala Ala Ile Val Arg Ala Glu Gly Glu Ser Glu
    210                 215                 220

Ser Ala Arg Leu Ile Ser Glu Ala Thr Ala Met Ala Gly Thr Gly Leu
225                 230                 235                 240

Ile Glu Leu Arg Arg Ile Glu Ala Ala Lys Glu Ile Ala Ala Glu Leu
                245                 250                 255

Ala Arg Ser Pro Asn Val Ala Tyr Ile Pro Ser Gly Glu Asn Gly Lys
                260                 265                 270

Met Leu Leu Gly Leu Asn Ala Thr Gly Phe Gly Arg
                275                 280
```

<210> SEQ ID NO 5
<211> LENGTH: 1133
<212> TYPE: DNA
<213> ORGANISM: Zea mays
<220> FEATURE:
<221> NAME/KEY: misc_feature
<222> LOCATION: (0)...(0)
<223> OTHER INFORMATION: Prohibitn - ZmPHB3

<400> SEQUENCE: 5

-continued

| | |
|---|---|
| caccaaacgg aatttcacat ccagcgagca ataccgcacc gcaggtaaga tcaaagagga | 60 |
| ggcgatggct ggcggcgggc aggcggcgat ttcgttcatg acgcggatgg cgaaggtggc | 120 |
| ggcggggttg ggcgtggcgg cgtccgcagc ctccacgtcc ttctacacgg tggacggcgg | 180 |
| agagcgcgcc gtcatcttcg atcgcgtccg cggcgtgctc ccgcgtacga tgtcagaggg | 240 |
| cacccatttg ctggtcccca tccttcagaa gcccttcatt ttcgacatcc gcactcgccc | 300 |
| tcacagcttc tcctccacct ccggcaccaa ggacctccag atggtcagcc tcacgctccg | 360 |
| cgtcctgtcg cgacccgacg tcgaacacct cccggacatc ttcacctccc tcgggctcga | 420 |
| gtacgacgag aaggtcctcc catccatcgg caacgaggtg ctcaaggccg tcgtcgcgca | 480 |
| gttcaacgcc gaccagctcc tcaccgagcg tccccacgtc tccgcgctcg tccgcgaatc | 540 |
| gctcaccaag cgcgcccgcg agttcaacat cgtcctcgac gaggtcgcca tcacccacct | 600 |
| agcctacggg caggagttcg cgcaggccgt cgagaagaag caggtcgcgc aacaggaggc | 660 |
| cgagcgctcc agattcctcg tcgcgcgcgc tgagcaggag aggcgcgccg ccatcgtccg | 720 |
| cgcagagggg gagagcgagg ccgcgcgcct tatctccgag gccacgacca ctgcgggcaa | 780 |
| cggcctgatc gagctcagga ggatcgaggc ggccaaggag atcgcaagcg ttctgtcgcg | 840 |
| cacgcccaac gtctcctaca tccccgccgg cgacaatggc cagatgctgc tcgggcttaa | 900 |
| cgccgcccgg tgaatggatc gtctttttcc cgcataatta gttagtagtg ccctattgaa | 960 |
| gtacttcagt aatttcagat gcatctactt agttatggtt ttgtggaacg attctatgct | 1020 |
| gggtaaagat ggtgatatgc attgctcata agttcggca gatggggaat ttgccagaat | 1080 |
| actctatcgt aatcacttat tgtgataaaa aaaaaaaaa aaaaaaaaa aaa | 1133 |

<210> SEQ ID NO 6
<211> LENGTH: 282
<212> TYPE: PRT
<213> ORGANISM: Zea mays

<400> SEQUENCE: 6

Met Ala Gly Gly Gln Ala Ala Ile Ser Phe Met Thr Arg Met Ala
1               5                   10                  15

Lys Val Ala Ala Gly Leu Gly Val Ala Ala Ser Ala Ala Ser Thr Ser
                20                  25                  30

Phe Tyr Thr Val Asp Gly Gly Glu Arg Ala Val Ile Phe Asp Arg Val
            35                  40                  45

Arg Gly Val Leu Pro Arg Thr Met Ser Glu Gly Thr His Leu Leu Val
        50                  55                  60

Pro Ile Leu Gln Lys Pro Phe Ile Phe Asp Ile Arg Thr Arg Pro His
65                  70                  75                  80

Ser Phe Ser Ser Thr Ser Gly Thr Lys Asp Leu Gln Met Val Ser Leu
                85                  90                  95

Thr Leu Arg Val Leu Ser Arg Pro Asp Val Glu His Leu Pro Asp Ile
                100                 105                 110

Phe Thr Ser Leu Gly Leu Glu Tyr Asp Glu Lys Val Leu Pro Ser Ile
            115                 120                 125

Gly Asn Glu Val Leu Lys Ala Val Val Ala Gln Phe Asn Ala Asp Gln
        130                 135                 140

Leu Leu Thr Glu Arg Pro His Val Ser Ala Leu Val Arg Glu Ser Leu
145                 150                 155                 160

Thr Lys Arg Ala Arg Glu Phe Asn Ile Val Leu Asp Glu Val Ala Ile
                165                 170                 175

-continued

```
Thr His Leu Ala Tyr Gly Gln Glu Phe Ala Gln Ala Val Glu Lys Lys
            180                 185                 190

Gln Val Ala Gln Gln Glu Ala Glu Arg Ser Arg Phe Leu Val Ala Arg
        195                 200                 205

Ala Glu Gln Glu Arg Arg Ala Ala Ile Val Arg Ala Glu Gly Glu Ser
    210                 215                 220

Glu Ala Ala Arg Leu Ile Ser Glu Ala Thr Thr Thr Ala Gly Asn Gly
225                 230                 235                 240

Leu Ile Glu Leu Arg Arg Ile Glu Ala Lys Glu Ile Ala Ser Val
                245                 250                 255

Leu Ser Arg Thr Pro Asn Val Ser Tyr Ile Pro Ala Gly Asp Asn Gly
            260                 265                 270

Gln Met Leu Leu Gly Leu Asn Ala Ala Arg
        275                 280
```

```
<210> SEQ ID NO 7
<211> LENGTH: 1148
<212> TYPE: DNA
<213> ORGANISM: Zea mays
<220> FEATURE:
<221> NAME/KEY: misc_feature
<222> LOCATION: (0)...(0)
<223> OTHER INFORMATION: Prohibitin - ZmPHB4

<400> SEQUENCE: 7
cccacgcgtc cgcccacgcg tccgcccacg cgtccggcct ccgccaccct accaactact     60
caataaccct agctaaaccc cacgccgccg cggcgacctc ctccgccggc aggatggaca    120
gcctcagggg agccaagttg ccgggcgtgc cgaagggcgg gagtgcgctc gtgaaggtgg    180
cgctgctcgg cggcgcgggg ctctacgccg tcctcaacag cttctacaac gtcgagggcg    240
gacaccgcgc catcgtcttc aaccgcctcg agggatcaa ggacaaggtg taccccgaag    300
gaactcacct gatgatcccg tggatcgaaa ggccgatcat ctacgacgtc cgcgcccgac    360
ccaacctcgt cgagagcacc tccggaagcc gcgacctcca gatggtgaga attggtcttc    420
gtgtccttac tcgaccatg ccagatcagc tacctaaaat ctacaggaac ctgggggaga    480
acttcaatga gagagttctg ccttcaatca ttcatgaaac actcaaagct gttgttgctc    540
aatacaatgc cagccagctg atcacccaga gagaggctgt gagcagggag attaggaaga    600
ttctgactga gagggccaac aacttcaata ttgctctgga tgatgtgtcc atcacaagcc    660
tcagctttgg aaaagagttt actcatgcca ttgaagccaa gcaggttgct gcacaagaag    720
ctgagcgtgc caagttcatt gttgagaagg ctgagcagga caagcgcagt gcagttatca    780
gggcacaggg tgaggctaag agcgcggagc tgattggcca agccattgcc aacaaccccg    840
ccttcctggc tctgagacag attgaagctg ccagggagat ctcccacacc atggcggcct    900
ccagcaacaa ggtgttcctt gattccaggg acctttttgct tggtcttcag cagctgaacg    960
tgggggcaa gcaaaagaag tgaagcggtc gtccccaggc catcgcggat gagagtagtt   1020
tcaggcgatg gttttatctg ttacagaatg cgcatgcgcg ggaatgaaca aagtggcacc   1080
atgttgcagt ctgtatgtac tgacaagttt gtctatctat ctttgattct caaaaaaaaa   1140
aaaaaaaa                                                           1148
```

```
<210> SEQ ID NO 8
<211> LENGTH: 289
<212> TYPE: PRT
<213> ORGANISM: Zea mays
```

```
<400> SEQUENCE: 8

Met Asp Ser Leu Arg Gly Ala Lys Leu Pro Gly Val Pro Lys Gly Gly
1               5                   10                  15

Ser Ala Leu Val Lys Val Ala Leu Leu Gly Gly Ala Gly Leu Tyr Ala
                20                  25                  30

Val Leu Asn Ser Phe Tyr Asn Val Glu Gly Gly His Arg Ala Ile Val
            35                  40                  45

Phe Asn Arg Leu Glu Gly Ile Lys Asp Lys Val Tyr Pro Glu Gly Thr
        50                  55                  60

His Leu Met Ile Pro Trp Ile Glu Arg Pro Ile Ile Tyr Asp Val Arg
65                  70                  75                  80

Ala Arg Pro Asn Leu Val Glu Ser Thr Ser Gly Ser Arg Asp Leu Gln
                85                  90                  95

Met Val Arg Ile Gly Leu Arg Val Leu Thr Arg Pro Met Pro Asp Gln
                100                 105                 110

Leu Pro Lys Ile Tyr Arg Asn Leu Gly Glu Asn Phe Asn Glu Arg Val
            115                 120                 125

Leu Pro Ser Ile Ile His Glu Thr Leu Lys Ala Val Val Ala Gln Tyr
        130                 135                 140

Asn Ala Ser Gln Leu Ile Thr Gln Arg Glu Ala Val Ser Arg Glu Ile
145                 150                 155                 160

Arg Lys Ile Leu Thr Glu Arg Ala Asn Asn Phe Asn Ile Ala Leu Asp
                165                 170                 175

Asp Val Ser Ile Thr Ser Leu Ser Phe Gly Lys Glu Phe Thr His Ala
                180                 185                 190

Ile Glu Ala Lys Gln Val Ala Ala Gln Glu Ala Glu Arg Ala Lys Phe
            195                 200                 205

Ile Val Glu Lys Ala Glu Gln Asp Lys Arg Ser Ala Val Ile Arg Ala
        210                 215                 220

Gln Gly Glu Ala Lys Ser Ala Glu Leu Ile Gly Gln Ala Ile Ala Asn
225                 230                 235                 240

Asn Pro Ala Phe Leu Ala Leu Arg Gln Ile Glu Ala Ala Arg Glu Ile
                245                 250                 255

Ser His Thr Met Ala Ala Ser Ser Asn Lys Val Phe Leu Asp Ser Arg
                260                 265                 270

Asp Leu Leu Leu Gly Leu Gln Gln Leu Asn Val Gly Gly Lys Gln Lys
            275                 280                 285

Lys
```